United States Patent
Metz et al.

(10) Patent No.: US 8,299,300 B2
(45) Date of Patent: Oct. 30, 2012

(54) METHOD FOR PREPARING DIFLUOROACETIC ACID AND SALTS THEREOF

(75) Inventors: François Metz, Irigny (FR); Laurent Saint-Jalmes, Vourles (FR)

(73) Assignee: Rhodia Operations, Aubervilliers (FR)

( * ) Notice: Subject to any disclaimer, the term of this patent is extended or adjusted under 35 U.S.C. 154(b) by 145 days.

(21) Appl. No.: 12/933,646

(22) PCT Filed: Mar. 9, 2009

(86) PCT No.: PCT/EP2009/052740
§ 371 (c)(1),
(2), (4) Date: Dec. 1, 2010

(87) PCT Pub. No.: WO2009/115426
PCT Pub. Date: Sep. 24, 2009

(65) Prior Publication Data
US 2011/0065955 A1    Mar. 17, 2011

(30) Foreign Application Priority Data
Mar. 19, 2008  (FR) ..................... 08 01513

(51) Int. Cl.
*C07C 53/18* (2006.01)
*C07C 51/60* (2006.01)

(52) U.S. Cl. ..................... 562/605; 562/852

(58) Field of Classification Search .................. None
See application file for complete search history.

(56) References Cited

U.S. PATENT DOCUMENTS

| 5,455,376 A | 10/1995 | Bielefeldt |
| 2005/0148649 A1 | 7/2005 | Billen et al. |

FOREIGN PATENT DOCUMENTS

| EP | 0694523 A | 1/1996 |
| EP | 0928783 | 7/1999 |
| GB | 976316 A | 11/1964 |
| WO | WO 9629298 | 9/1996 |
| WO | WO 0035834 | 6/2000 |

OTHER PUBLICATIONS

European Patent Office: International Search Report; International Application No. PCT/EP2009/052740, mailed Jun. 5, 2009.

*Primary Examiner* — Paul A Zucker
(74) *Attorney, Agent, or Firm* — Hunton & Williams, LLP

(57) ABSTRACT

The invention relates to a method for preparing difluoroacetic acid and the salts thereof. The invention also relates to the preparation of difluoroacetyl fluoride used as an intermediate product in the preparation of difluoroacetic acid. The method for preparing difluoroacetic acid according to the invention is characterized in that the same comprises the step of preparing difluoroacetyl fluoride by reacting dichloroacetyl chloride with hydrofluoric acid in a gaseous phase and in the presence of a chromium-based catalyst, followed by the step of hydrolysing the difluoroacetyl fluoride thus obtained.

19 Claims, No Drawings

METHOD FOR PREPARING DIFLUOROACETIC ACID AND SALTS THEREOF

CROSS-REFERENCE TO RELATED APPLICATIONS

This application is the U.S. National Phase of International Application Number PCT/EP2009/052740 filed on Mar. 9, 2009, which claims priority to French Application No. FR 0801513, filed Mar. 19, 2008, both of which are incorporated by reference herein in their entireties.

FIELD OF THE INVENTION

The present invention relates to a process for preparing difluoroacetic acid and salts thereof.

The invention is also directed toward the preparation of difluoroacetyl fluoride, which is used as an intermediate product in the manufacture of difluoroacetic acid.

More specifically, the invention relates to a process for preparing difluoroacetyl fluoride, in the gas phase.

BACKGROUND

Various methods exist for preparing difluoroacetic acid or salts thereof.

In particular, it is known practice to prepare difluoroacetic acid according to a chlorine-fluorine exchange reaction, by reacting potassium fluoride with dichloroacetic acid derivatives, for example N,N-diethylchlorofluoroacetamide (Chemical Abstracts 88, (1), 6300 m) or N-pyrrolidine-chlorofluoroacetamide (Chemical Abstracts 108, (19), 166949q).

An entirely different method for obtaining difluoroacetic acid lies in an oxidation reaction of difluoroethanol obtained by hydrolysis of 1-bromo-2,2-difluoroethane [Y. Désirant, Bull. Sci. Acad. Roy. Belg. [5] 15, 966-82 (1929)].

Another synthetic route is based on a dehydrohalogenation reaction starting with monochlorodifluoroacetic acid. Mention may be made in particular of U.S. Pat. No. 5,455,376, which describes the production of difluoroacetic acid via the gas-phase hydrogenation of monochlorodifluoroacetic acid, in the presence of a catalyst based on a noble metal, palladium or platinum, deposited on a support, for example alumina.

There is also a preparation process described in EP 1 137 615, via liquid-phase hydrogenation in a sodium hydroxide medium of monochlorodifluoroacetic acid, in the presence of Raney nickel. The chemical yield is good, but the production efficiency of such a process needs to be improved. There may be formation, as a side product, of monofluoroacetic acid, which is a particularly toxic product. Moreover, the acid obtained is in a sodium form, which is difficult to recover from the reaction medium.

SUMMARY OF THE INVENTION

The aim of the invention is to propose a process for preparing difluoroacetic acid that uses a starting substrate of different nature.

A process has now been found, and this is what constitutes the subject of the present invention, for preparing difluoroacetic acid, characterized in that it comprises a step of preparing difluoroacetyl fluoride by reacting dichloroacetyl chloride and hydrofluoric acid, in the gas phase, in the presence of a chromium-based catalyst, followed by a step of hydrolyzing the difluoroacetyl fluoride obtained.

Another subject of the invention is the process for preparing difluoroacetyl fluoride.

Another subject of the invention is the process for preparing difluoroacetic acid salts.

DETAILED DESCRIPTION OF PREFERRED EMBODIMENTS

A chromium-based fluorination catalyst is involved in the process of the invention.

The catalyst used preferably comprises oxides, halides, oxyhalides or mineral salts of chromium optionally doped with a metal element, for instance nickel, cobalt, magnesium or zinc.

It is preferentially a chromium oxide, a chromium fluoride or a chromium oxyfluoride, or alternatively chromium doped with a metal element, for instance nickel or magnesium.

The catalyst may undergo activation by a heat treatment and/or a fluorination treatment. In particular, the activation may take place during the fluorination. The temperature is advantageously chosen between 100° C. and 400° C., preferably between 200° C. and 300° C.

The chromium is used in particular in the form of oxides with different degrees of oxidation and/or in the form of hydroxides in powder or gel form.

It is possible to use an activated chromium III oxide prepared, for example, by precipitation of water-soluble chromium III salts, for example chlorides, nitrates, acetates or sulfates using an alkali metal hydroxide, preferably sodium or potassium hydroxide, or ammonium hydroxide. The precipitate is dried at about 110° C. and calcined at a temperature below 700° C., preferably between 400 and 600° C.

Anhydrous chromium oxide may be obtained by calcination of inorganic chromium salts such as ammonium chromate or chromium nitrate or by calcination of organic chromium salts, for instance chromium oxalates or formates at 350° C., under a nitrogen atmosphere.

Use may be made especially of a catalyst of Cr—Ni type, with a chromium valency of between 2 and 3 and a nickel valency of between 0 and 2, the amount of nickel expressed as an atomic percentage representing from 0.1% to 10%.

One method for preparing this catalyst consists in performing a thermal decomposition, separately or as a mixture of one or more organic chromium salts (for example oxalate) and of one or more nickel salts (for example oxalate), forming the mixture and then fluorinating the formed catalyst.

The thermal decomposition generally takes place between 370° C. and 400° C., under an atmosphere of inert gas, for example nitrogen.

The forming of the catalyst obtained may be performed, under non-oxidative conditions, for example by extrusion, and the formed product is then dried at about 120° C.-130° C., and then calcined at 370° C.-400° C., under an inert atmosphere.

The catalyst is heated to between 100° C. and 500° C., under hydrofluoric acid, for between 1 and 12 hours.

A catalyst of Cr—Mg type may also be used.

It may be obtained especially by mixing a chromium salt (for example nitrate) in solution with a magnesium oxide or hydroxide, prolonged drying for between 12 and 24 hours, for example at 100° C., and then activation with hydrofluoric acid, for example at 200° C.

The active phase may be provided in a finely divided form, or alternatively formed or deposited on a support.

Examples of supports that may be mentioned include silica, alumina, zirconia and titanium oxide. Preferably, the chromium is deposited on a support in a proportion of 0.5% to 5% of the weight of the catalyst.

The catalysts may be present in various forms in the process of the invention: powder, formed products such as granules (for example extrudates or beads), pellets, which are obtained by extrusion, molding, compacting or any other type of known process. In practice, at the industrial level, it is the granule or bead forms that offer the greatest advantages, both as regards the efficacy and as regards the ease of use.

In accordance with the process of the invention, a fluorination reaction is performed in a first step by reacting dichloroacetyl chloride and hydrofluoric acid, in the gas phase, in the presence of the fluorination catalyst.

The ratio between the hydrofluoric acid and the dichloroacetyl chloride may vary widely. Generally, the hydrofluoric acid is in excess amount. Thus, the ratio between the number of moles of hydrofluoric acid and the number of moles of dichloroacetyl chloride usually ranges between 1 and 30. It is advantageously chosen between 6 and 10.

The process in accordance with the invention is performed at a high temperature, generally above 200° C. It is recommended to work at temperatures of between 250° C. and 400° C. and preferably between 250° C. and 300° C.

For reasons of simplicity, the process of the invention is performed at atmospheric pressure. However, it is also possible to work at lower or higher pressures.

From a practical point of view, the process may be performed in batch or continuous mode.

To begin with, the dichloroacetyl chloride and the hydrofluoric acid are mixed together in any manner.

Said reagents may thus be mixed together in a mixing zone, and the mixture obtained may then be conveyed onto the catalytic bed.

When the process is performed in batch mode, the amount of fluorination catalyst used, expressed as weight of catalyst per weight of dichloroacetyl chloride, may vary, for example, between 0.5% and 20% and preferably between 0.5% and 5%.

The other variant of the invention consists in performing the reaction in continuous mode, in a tubular reactor comprising the solid catalyst arranged as a fixed bed.

The dichloroacetyl chloride and the hydrofluoric acid may be introduced separately or as a mixture into the reactor. As mentioned previously, they may be mixed together in a mixing zone, and the mixture obtained may then be conveyed onto the catalytic bed.

The reaction mixture passes through the catalytic bed, preferably from the bottom upward.

The contact time, which is defined as the ratio between the apparent volume of catalyst and the flow rate of the gas stream, may vary widely, and is usually between 0.2 and 100 seconds. The contact time is preferably chosen between 5 and 50 seconds.

The weight of substrate used per weight of catalyst and per hour generally ranges between $0.01\ h^{-1}$ and $2\ h^{-1}$ and preferably between $0.05\ h^{-1}$ and $0.5\ h^{-1}$.

At the end of the reaction, a gas phase comprising the difluoroacetyl fluoride, the excess hydrofluoric acid and the hydrochloric acid formed by the reaction is recovered.

In accordance with the process of the invention, a step of hydrolysis of the difluoroacetyl fluoride to difluoroacetic acid is then performed.

To this end, the gas stream is placed in contact with water. The amount of water used is at least equal to the stoichiometric amount.

Generally, the operation is performed by sending, the gas stream into a hydrolysis column: the water being sent in counter-currentwise relative to the gas stream which rises from the bottom upward in the column.

It is also possible to perform an acidic hydrolysis, for example by using a solution of a strong mineral acid, for example hydrochloric acid at 30% by weight.

Thus, the difluoroacetic acid is recovered at the bottom of the column and hydrogen chloride gas is recovered at the top of the column.

Difluoroacetic acid salts may be readily manufactured from the acid, especially by reaction with a base, preferably sodium hydroxide or potassium hydroxide.

The process of the invention is advantageously performed in apparatus capable of withstanding the corrosion caused by the hydrofluoric acid. To this end, materials such as, for example, vitrified steels or Hastelloy® steels are chosen.

According to one variant of the invention, the difluoroacetyl fluoride is recovered from said gas stream comprising the difluoroacetyl fluoride, the excess hydrofluoric acid and the hydrochloric acid formed by the reaction, by condensing said gas stream by lowering its temperature to between −40° C. and 10° C. and preferably between −20° C. and 0° C. and then by distilling the condensed stream.

The process of the invention is particularly advantageous since it uses a cheap starting material and has good production efficiency.

The examples that follow illustrate the invention without, however, limiting it.

The abbreviations have the following meanings:
DCAC: dichloroacetyl chloride
DFAF: difluoroacetyl fluoride In the examples, the degree of conversion and the yields obtained are defined.

The degree of conversion (DC) corresponds to the ratio between the number of moles of DCAC substrate converted and the number of moles of DCAC substrate employed.

The yield (RY) corresponds to the ratio between the number of moles of DFAF product formed and the number of moles of DCAC substrate employed.

The yield (CY) corresponds to the ratio between the number of moles of DFAF product formed and the number of moles of DCAC substrate converted.

EXAMPLES

The operating protocol that is followed in the various examples is given below.

The reaction is performed in a reactor made of Hastelloy C276, which is a nickel-based alloy (57% by weight) comprising 16% chromium, 16% molybdenum, 5% iron, 4% tungsten, 2.5% cobalt, 1% manganese, 0.35% vanadium, 0.08% silicon and 0.01% carbon.

Predistilled dichloroacetyl chloride (DCAC) is introduced at a flow rate of 0.11 mol/h (~15 g/h) and anhydrous HF is introduced at a flow rate of 1.1 to 2.6 mol/h (22 to 52 g/h) into a Hastelloy C276 reactor formed of a tube 60 cm long with an outside diameter of 2.5 cm, filled with a catalyst based on chromium III oxide (~150 g) predried to constant weight and fluorinated (24 hours at 250° C.).

According to the test, the temperature is set from 200° C. to 350° C., as an isotherm or gradient.

Under these conditions, the residence time $t_r$ ranges between 10 and 20 seconds.

After reaction, the difluoroacetyl fluoride (DFAF) is assayed by converting it into the form of the potassium salt of difluoroacetic acid.

The exiting stream is hydrolyzed in potassium hydroxide spargers mounted in series, and the various acids are assayed in the form of potassium salts by ion chromatography.

Examples 1 to 9

The examples that follow illustrate the effect of the temperature, the HF/DCAC ratio and the residence time.

TABLE I

| Ref. Ex. | T °C. | $t_r$ | HF/DCAC | $DC_{DCAC}$ % | $RY_{DFAF}$ % | $CY_{DFAF}$ % |
|---|---|---|---|---|---|---|
| 1 | 250 | 20 | 11.3 | 66 | 30 | 45 |
| 2 | 250 | 20 | 11.7 | 68 | 33 | 48 |
| 3 | 250 | 20 | 11.6 | 72 | 32 | 45 |
| 4 | 200 | 20 | 10.2 | 22 | 3 | 14 |
| 5 | 200 | 20 | 11.4 | 18 | 3 | 17 |
| 6 | 200 to 250 | 20 | 11.5 | 32 | 17 | 53 |
| 7 | 300 | 11 | 18.5 | 40 | 5 | 12.5 |
| 8 | 300 | 20 | 10 | 60 | 20 | 33 |
| 9 | 350 | 19 | 10 | 85 | 20 | 25 |

The invention claimed is:

1. A process for preparing difluoroacetic acid, comprising: reacting dichloroacetyl chloride and hydrofluoric acid, in the gas phase, and in the presence of a chromium-based fluorination catalyst, to form difluoroacetyl fluoride; and hydrolyzing the difluoroacetyl fluoride to yield difluoroacetic acid.

2. The process of claim 1, wherein the fluorination catalyst comprises an oxide, halide, oxyhalide, mineral salt of chromium optionally doped with a metal element, or a mixture thereof.

3. The process of claim 2, wherein the fluorination catalyst comprises a chromium oxide, a chromium fluoride, a chromium oxyfluoride, chromium doped with a metal element, or a mixture thereof.

4. The process of claim 1, further comprising activating the catalyst via a heat treatment and/or a fluorination treatment, wherein the activation optionally occurs during the fluorination step.

5. The process of claim 1, wherein the catalyst comprises a chromium III oxide that has optionally been activated via a fluorination treatment.

6. The process of claim 1, wherein an active phase of the catalyst is finely-divided or is formed or deposited on a support.

7. The process of claim 6, wherein the catalyst comprises chromium deposited on a support in an amount ranging from 0.5% to 5% of the weight of the catalyst.

8. The process of claim 1, wherein the mole ratio of hydrofluoric acid to dichloroacetyl chloride ranges from 1 to 30.

9. The process of claim 1, wherein the reaction temperature ranges from 250° C. to 400° C.

10. The process of claim 1, wherein the process is performed in continuous mode.

11. The process of claim 1, wherein the reaction is performed in continuous mode in a tubular reactor comprising a fixed bed comprising the catalyst in solid form.

12. The process of claim 1, wherein reacting the dichloroacetyl chloride and hydrofluoric acid comprises mixing the dichloroacetyl chloride and hydrofluoric acid in a mixing zone before conveying the mixture onto a catalytic bed.

13. The process of claim 1, wherein the contact time ranges from 0.2 to 100 seconds.

14. The process of claim 1, wherein the weight of substrate used per weight of catalyst per hour ranges from 0.01 $h^{-1}$ to 2 $h^{-1}$.

15. The process of claim 1, further comprising:
recovering a gaseous phase comprising the difluoroacetyl fluoride, the excess hydrofluoric acid, and hydrochloric acid formed by the reaction.

16. The process of claim 1, wherein the hydrolyzing step comprises contacting a gas stream comprising difluoroacetyl fluoride with water.

17. The process of claim 1, further comprising:
reacting the difluoroacetic acid with a base.

18. A process for preparing difluoroacetyl fluoride comprising:
reacting dichloroacetyl chloride and hydrofluoric acid, in the gas phase, in the presence of a chromium-based catalyst.

19. The process of claim 1, wherein the process is performed in batch mode.

* * * * *